(12) United States Patent
Peters et al.

(10) Patent No.: US 10,180,409 B2
(45) Date of Patent: Jan. 15, 2019

(54) METHOD FOR MANUFACTURING A SOLID ELECTROLYTE SENSOR ELEMENT FOR DETECTING AT LEAST ONE PROPERTY OF A MEASURING GAS IN A MEASURING GAS CHAMBER, CONTAINING TWO POROUS CERAMIC LAYERS

(71) Applicant: Robert Bosch GmbH, Stuttgart (DE)

(72) Inventors: Christoph Peters, Stuttgart (DE);
Thomas Moser, Schwieberdingen (DE);
Tobias Kuehnlein, Zapfendorf (DE);
Lothar Diehl, Gemmrigheim (DE);
Harald Guenschel, Gerach (DE)

(73) Assignee: Robert Bosch GMBH, Stuttgart (DE)

( * ) Notice: Subject to any disclaimer, the term of this patent is extended or adjusted under 35 U.S.C. 154(b) by 211 days.

(21) Appl. No.: 14/775,264

(22) PCT Filed: Jan. 10, 2014

(86) PCT No.: PCT/EP2014/050348
§ 371 (c)(1),
(2) Date: Sep. 11, 2015

(87) PCT Pub. No.: WO2014/139691
PCT Pub. Date: Sep. 18, 2014

(65) Prior Publication Data
US 2016/0061767 A1    Mar. 3, 2016

(30) Foreign Application Priority Data

Mar. 12, 2013 (DE) .................. 10 2013 204 204

(51) Int. Cl.
*G01N 27/407* (2006.01)
*G01N 27/406* (2006.01)

(52) U.S. Cl.
CPC ..... *G01N 27/4074* (2013.01); *G01N 27/4077* (2013.01); *G01N 27/4067* (2013.01); *G01N 27/4071* (2013.01)

(58) Field of Classification Search
CPC .. G01M 15/10; G01M 15/102; G01M 15/104; G01N 27/404–27/407;
(Continued)

(56) References Cited

U.S. PATENT DOCUMENTS 5,160,598 A * 11/1992 Sawada ................ G01N 27/407
204/429
5,593,558 A    1/1997 Sugino et al.
(Continued)

FOREIGN PATENT DOCUMENTS

DE    102012202716    8/2012
EP    1775580    4/2007

OTHER PUBLICATIONS

Material Data Sheet on Silicon Carbide.*
(Continued)

*Primary Examiner* — Gurpreet Kaur
(74) *Attorney, Agent, or Firm* — Norton Rose Fulbright US LLP; Gerard Messina

(57) ABSTRACT

A method for manufacturing a sensor element is provided for detecting at least one property of a measuring gas in a measuring gas chamber, in particular for detecting a proportion of a gas component in the measuring gas or a temperature of the measuring gas. The method includes the following steps: providing at least one solid electrolyte which includes at least one functional element; applying, at least in sections, at least one first layer made of a ceramic material to the solid electrolyte, the first layer having a first porosity after the application; and applying, at least in sections, at least one second layer made of a ceramic
(Continued)

material, the second layer having a second porosity after the application, and the first layer differing from the second layer with respect to at least one material property. Moreover, a sensor element which is manufacturable according to this method is provided.

15 Claims, 2 Drawing Sheets

(58) Field of Classification Search
CPC .... G01N 27/409; G01N 27/419; G01N 27/41; F01N 2560/00–2560/20; F01N 2550/00–2550/24
See application file for complete search history.

(56) References Cited

U.S. PATENT DOCUMENTS

| | | | |
|---|---|---|---|
| 5,948,966 A * | 9/1999 | Takahashi | F01N 11/00 204/424 |
| 6,409,899 B1 | 6/2002 | Satou et al. | |
| 2008/0054158 A1 | 3/2008 | Ariyur et al. | |
| 2009/0221414 A1 * | 9/2009 | Glaubitt | C04B 35/111 501/80 |
| 2010/0155240 A1 * | 6/2010 | Matsuoka | G01N 27/4077 204/424 |
| 2010/0243445 A1 | 9/2010 | Shindo et al. | |
| 2011/0003228 A1 * | 1/2011 | Zerfass | F16J 15/102 429/452 |
| 2011/0287340 A1 * | 11/2011 | Mougin | C25B 9/00 429/514 |
| 2013/0316167 A1 * | 11/2013 | Yager | C23C 16/26 428/336 |
| 2015/0377823 A1 * | 12/2015 | Akasaka | G01N 27/4065 204/406 |

OTHER PUBLICATIONS

Material Data Sheet on Silicon Oxide.*
International Search Report for PCT/EP2014/050348, dated Mar. 20, 2014.
Thermal Spray Materials and Applications, Ch. 2.1.3 "Thermal spray nanostructured powder material", (2008), Editor WAND, Naijun, publ. National Defense Industry Press, 1st Ed., pp. 16-26.

* cited by examiner

METHOD FOR MANUFACTURING A SOLID ELECTROLYTE SENSOR ELEMENT FOR DETECTING AT LEAST ONE PROPERTY OF A MEASURING GAS IN A MEASURING GAS CHAMBER, CONTAINING TWO POROUS CERAMIC LAYERS

BACKGROUND INFORMATION

Numerous sensor elements and methods for detecting at least one property of a measuring gas in a measuring gas chamber are known from the related art. This may basically involve any physical and/or chemical properties of the measuring gas, and one or multiple properties may be detected. The present invention is described below in particular with regard to a qualitative and/or quantitative detection of a proportion of a gas component in the measuring gas, in particular with regard to a detection of an oxygen content in the measuring gas. The oxygen content may be detected in the form of a partial pressure and/or in the form of a percentage, for example. Alternatively or additionally, however, other properties of the measuring gas, such as the temperature, are also detectable.

For example, sensor elements of this type may be designed as so-called lambda sensors, as are known, for example, from Konrad Reif (Ed.): Sensoren im Kraftfahrzeug [Automotive Sensors], 1st Edition 2010, pp. 160-165. Using broadband lambda sensors, in particular planar broadband lambda sensors, the oxygen concentration, for example, in the exhaust gas may be determined over a wide range, and the air-fuel ratio in the combustion chamber may thus be deduced. The excess air factor $\lambda$ describes this air-fuel ratio.

In particular ceramic sensor elements are known from the related art which are based on the use of electrolytic properties of certain solid bodies, i.e., based on ion-conducting properties of these solid bodies. In particular, these solid bodies may be ceramic solid electrolytes, for example zirconium dioxide ($ZrO_2$), in particular yttrium-stabilized zirconium dioxide (YSZ) and scandium-doped zirconium dioxide (ScSZ), which may contain small additions of aluminum oxide ($Al_2O_3$) and/or silicon oxide ($SiO_2$).

Increasing functional requirements are being imposed on such sensor elements. In particular, rapid operational readiness of lambda sensors after starting the engine plays a large role. This is influenced essentially by two aspects. The first aspect concerns rapid heating up of the lambda sensor to its operating temperature, which is customarily above 600° C., which may be achieved by an appropriate design of a heating element or a reduction in size of the area to be heated. The other aspect concerns the robustness against thermal shock due to hydrolock during operation. This thermal shock is based on the fact that the temperature in the exhaust pipe is below the dew point of water for a certain period after starting the engine, so that the water vapor which forms during the combustion of fuel may condense in the exhaust pipe. This results in the formation of water droplets in the exhaust pipe. The heated-up ceramic of the lambda sensor may be damaged or even destroyed due to thermal stresses or ruptures in the sensor ceramic due to the impact of water droplets.

For this reason, lambda sensors have been developed which have a porous protective ceramic layer on their surface, also referred to as a thermal shock protective layer. This protective layer ensures that water droplets which strike the lambda sensor are distributed over a large surface area, and therefore the localized temperature gradients occurring in the solid-state electrolyte or the sensor ceramic are reduced. In the heated state, these lambda sensors thus tolerate a certain size of condensation water droplets without being damaged. The protective layer is customarily applied to the sensor element in an additional method step. Various materials, for example aluminum oxide or spinel ($MgAl_2O_4$), and application techniques, for example spraying or dipping processes, are used for this purpose. For example, it is known to apply a uniformly thick thermal shock protective layer made of porous aluminum oxide with the aid of atmospheric plasma spraying. With this type of thermal coating process, introduced particles are melted and are accelerated onto the solid electrolyte surface, so that the thermal shock protective layer is applied to the entire solid electrolyte surface. In the low-temperature range, i.e., in a temperature range of approximately 300° C. to 400° C., due to its limited permeability the thermal shock protective layer reduces the entry of water into the solid electrolyte of the sensor element, which is made at least partially of zirconium dioxide, and in the high-temperature range, i.e., in a temperature range of approximately 400° C. to 600° C., limits the cooling via heat conduction. At higher temperatures, the Leidenfrost effect prevents cooling.

Despite the numerous advantages of the methods known from the related art for manufacturing sensor elements for lambda sensors, these methods still have the potential for improvement. In order to not influence the functionality of the sensor element and at the same time to reliably protect against water droplets, for example from the exhaust gas flow of an internal combustion engine, the thickness and the porosity of the thermal shock protective layer must be optimally selected. Optimizing the sensor element with regard to the two mentioned influencing variables results in various conflicting objectives. Thus, a thick thermal shock protective layer reliably protects against hydrolock, but as additional mass, adversely affects the heat-up behavior of the sensor element. The thermal shock protective layer impairs the dynamics of the lambda sensor. In addition, the use of aluminum oxide as a thermal shock protective layer material having good heat conductivity may result in increased heat discharge from the sensor element. Lastly, although slimming down the ceramic substrate allows quicker heat-up times, it makes the sensor element more mechanically fragile. In addition, the sprayed layers are relatively inhomogeneous, so that the layers must be sprayed on more thickly than necessary in order to be sufficiently stable against thermal shock. Moreover, the open porosity of plasma-sprayed layers changes due to thermal aging, so that the functioning of "voltage-jump" sensors as well as broadband sensors having a covered gas inlet port is impaired. The connection between the sensor element and the layer provided by the inherent bond of the thermal shock protective layer is not entirely satisfactory. In addition, the thermal shock protective layer represents an additional diffusion barrier through which the measuring gas, which contains water vapor and carbon dioxide, for example, must diffuse in order to reach the outer electrode.

SUMMARY

Therefore, a method for manufacturing a sensor element for detecting at least one property of a measuring gas in a measuring gas chamber as well as a sensor element which is manufacturable according to this method are provided which at least largely avoid the disadvantages of known methods and sensor elements, in which the robustness against thermal shock may be improved without increasing the thermal mass, and without causing prior damage.

The method according to the present invention includes the following steps, preferably in the stated sequence:
  providing at least one solid electrolyte which includes at least one functional element,
  applying, at least in sections, at least one first layer made of a ceramic material to the solid electrolyte, the first layer having a first porosity after the application, and
  applying, at least in sections, at least one second layer made of a ceramic material, the second layer having a second porosity after the application, and the first layer differing from the second layer with respect to at least one material property.

The material property may be selected from the group composed of: porosity, heat conductivity, coefficient of thermal expansion, and heat capacity. The first layer and the second layer may be made of different materials. Alternatively, a design of identical materials which are treated differently in the course of further processing is possible. The first porosity may be greater than the second porosity. A continuous transition of the porosity from the first layer to the second layer, and thus a porosity gradient, is also possible. The first layer may have a lower heat capacity than the second layer. The first and/or the second layer may be produced or applied by thermal spraying, for example plasma spraying, dipping, spraying, printing methods, or doctor blade coating methods. One or multiple layers may be applied to the sintered sensor element. One or multiple layers may be applied to the unsintered sensor element. The first layer and/or the second layer may be made of a sol. For example, a ceramic slurry or a sol including ceramic fillers may be used for the dip and/or spray coating. The method may also include at least one thermal treatment step for the solid electrolyte after the application of the spray and/or dip coating. The thermal treatment step may be carried out at a temperature of 40° C. to 120° C., preferably 50° C. to 100° C., for example 75° C. The annealing step may be carried out at a temperature of 1,000° C. to 1,300° C., preferably 1,100° C. to 1,200° C., for example 1,150° C. The solid electrolyte may also include a heating element for heating the solid electrolyte, the heating element carrying out the annealing step. The first layer may be applied with the aid of atmospheric plasma spraying. The second layer may be applied by thermal treatment, in particular melting, of a surface of the first layer facing away from the solid electrolyte.

A sensor element according to the present invention for detecting at least one property of a measuring gas in a measuring gas chamber, in particular for detecting a proportion of a gas component in the measuring gas chamber or a temperature of the measuring gas, may include at least one solid electrolyte which includes at least one functional element, at least one first layer, made of a ceramic material, on the solid electrolyte, the first layer having a first porosity, and at least one second layer made of a ceramic material, the second layer having a second porosity and differing with respect to at least one material property. For example, the first porosity may be greater than the second porosity.

Within the scope of the present invention, a solid electrolyte is understood to mean a body or object having electrolytic properties, i.e., having ion-conducting properties. In particular, a solid electrolyte may be a ceramic solid electrolyte. This also includes the raw material of a solid electrolyte, and therefore the design as a so-called green compact or brown compact, which becomes a solid electrolyte only after sintering.

Within the scope of the present invention, a functional element is understood to mean an element which is selected from the group composed of: electrode, conductor track, diffusion barrier, diffusion gap, reference gas channel, heating element, Nernst cell, and pump cell. In particular, functional elements are understood to mean those elements which meet the essential chemical and/or physical and/or electrical and/or electrochemical functions of a lambda sensor.

Within the scope of the present invention, a sol is understood to mean a colloidal dispersion m composed of precursors of ceramic materials, in particular of metal oxides. Within the scope of the present invention, the precursors of metal oxides are understood to mean in particular metal alcoholates and metal carboxylates. Precursors of this type are converted into metal oxides by thermal treatment. The base reactions which proceed are hydrolysis and condensation. Metal hydroxide groups are formed from metal alcoholates and water, under separation of alcohol molecules. Analogous reactions may be formulated for metal carboxylates or metal diketonates; however, these groups have a much higher hydrolytic stability. The metal hydroxide groups of hydrolyzed precursor molecules condense with one another, under separation of water. Trimers, tetramers, and further oligomers are formed from the dimer in the manner of an inorganic polycondensation reaction, until ultimately a particle has formed. Depending on the solvent, a distinction is made between alcoholic sols and hydrosols; in particular hydrosols are usable within the scope of the present invention. Continued particle growth and the aggregation of sol particles to form secondary particles result in an increase in viscosity. As soon as a network composed of sol particles has formed, this is referred to as gelling. The viscous sol is subsequently transformed into a viscoelastic solid body. The gel is composed of a gel framework and the solvents which it encloses, but with all pores being connected to one another. One example of a sol which may be used within the scope of the present invention is described in DE 10 2006 011 224 B4, and is incorporated by reference herein.

Within the scope of the present invention, an application of the coating in sections is understood to mean an application of the coating in which an outer surface or surface of the solid electrolyte or a layer already applied thereto is at least partially covered by the subsequent layer without necessarily being completely covered. It is therefore possible to apply the coating only to certain sections of the solid electrolyte, for example only to certain side areas or side edges, or only in a certain area of the solid electrolyte, which, viewed in a direction of longitudinal extension, for example, of the sensor element, is situated farther in the measuring gas chamber than other areas of the solid electrolyte.

Within the scope of the present invention, a porosity is understood to mean the ratio of the cavity volume to the total volume of a substance or substance mixture as a dimensionless measuring variable. This measuring variable may be expressed in particular in percent. An open porosity is understood to mean the proportion of the cavity volume, of the total cavity volume, of those cavities which are connected to one another and to the ambient air. A "certain porosity" is understood to mean a porosity of at least 20%, preferably at least 30%, and more preferably at least 40%, for example 60%. A porosity above 80% is not included for technical reasons, since it may lower the stability of the layer.

Within the scope of the present invention, an annealing step is understood to mean the heating of the solid electrolyte and of the sol or the ceramic slurry to a temperature below the melting temperature of the materials of the solid electrolyte and of the sol.

Within the scope of the present invention, a pore-forming agent is understood to mean any material which is constituted for making the ceramic layer, applied by dipping or spraying, porous and more lightweight. Examples include sawdust, cork flour, starch, coal dust, polymer beads, or polymer fibers, in particular short fibers. In particular, carbon-based materials are understood to mean materials which combust during so-called sintering and leave cavities behind.

A basic concept of the present invention is to provide a multi-ply or multi-layer thermal shock protective layer which may be optimally adapted to certain requirements, for example thermal shock protection, heat conductivity, heat capacity, water permeability, or wettability. Due to the thermal shock protective layer, the properties of the individual layers are set in such a way that impairment of the functioning of the sensor element is largely avoided or reduced. In particular, advantages result for the fast light-off time and for the heating voltage requirements. Due to the great fluctuations in the layer thickness, the average layer thickness in conventional thermal shock protective layers must be increased in order to ensure the necessary minimum layer thickness. The heat capacity for conventional sensor elements is thus increased in such a way that rapid switch-on of the sensor element, i.e., so-called fast light-off, is slowed down, for example by approximately 2.2 seconds or 1.4 seconds, as a function of the particular sensor model.

Due to a thermal shock protective layer being made of multiple individual layers which are optimally adapted to particular requirements, for example thermal shock protection, heat conductivity, water permeability, heat capacity, and wettability, the impairment of the functioning and dynamics of the lambda sensor may be reduced by the applied thermal shock protective layer. For example, the layers may differ with respect to their porosity. At the same time, however, by varying the selected ceramic, for example with an inner layer of zirconium dioxide and an outer layer of aluminum oxide, the heat conductivity and the heat capacity may also be adapted, partially independently of the porosity. The layer thickness and the thermal mass of the thermal shock protective layer may thus be kept preferably small. In addition, a high porosity of the inner thermal shock protective layer may thus be achieved, as the result of which the thermal mass of the thermal shock protective layer is decoupled from the sensor element. The heating voltage requirement and the fast light-off time may be reduced by the thermal decoupling of the inner thermal shock protective layer. The permeability of water may be reduced by the use of a thin, finely porous outer layer; i.e., the layer becomes hydrophobic without the measuring gas entry to the measuring electrodes being impermissibly reduced. In other words, the outer layer has the function of a diaphragm. In particular, the inlet area of a gas inlet port of the base ceramic of the sensor element is significantly enlarged by the roughly porous inner layer of the thermal shock protective layer, and therefore the gas inlet restriction by the outer, comparatively more dense thermal shock protective layer is effectively decreased. For a manufacturing variation of the permeability of the outer layer, this results in even smaller variations in the gas inlet, and thus in the increase of the characteristic curve of the sensor element. Due to the use of various ceramics, the thermal properties, for example heat conductivity, thermal expansion, and heat capacity, may be set as a partial function of the porosity. In addition, the thermomechanical stresses between the sensor element and the thermal shock protective layer may be reduced, so that no change in the porosity occurs due to microcracks, or macroscopic cracks do not result in failure of the thermal shock protective layer or of the sensor element. The dynamic response characteristic of the sensor element during rapid gas exchanges may thus be improved, since the gas storage capacity of the thin inner, highly porous thermal shock protective layer is reduced due to the smaller open pore volume.

Another basic concept of the present invention is to optimize the thermal shock protective layer by inorganic porous layers on ceramic exhaust gas sensors. The structure of the thermal shock protective layer is adapted to the dynamics and the thermal shock protection in a targeted manner. A design of the thermal shock protective layer is particularly advantageous in which the inner layer has a high porosity. This should be achieved by the uniform distribution of large pores. The outer layer of the thermal shock protective layer is made up of a layer having a lower, finely distributed porosity. Accordingly, the high porosity of the inner thermal shock protective layer represents a very good thermal insulation between the solid electrolyte and the rest of the thermal shock protective layer, since, due to the high proportion of pores which contain large quantities of air, the heat conductivity is low compared to the solid electrolyte. The solid electrolyte may therefore be heated up more rapidly; i.e., a shorter fast light-off time is achieved since the mass of the thermal shock protective layer is thermally decoupled from the solid electrolyte. The decoupling of the thermal masses of the thermal shock protective layer from the solid electrolyte also results in a lower heating voltage requirement, since the cooling of the thermal shock protective layer is not directly transferred to the surface of the solid electrolyte. A smooth surface with little roughness is achieved by setting a fine porosity of the outer layer. This prevents the penetration of water into the protective layer, which would increase the fast light-off time. There is also an improved thermal shock robustness on account of the reduced water permeability due to producing a smooth surface. To allow water which has penetrated into the thermal shock protective layer to be able to escape during rapid heat-up of the solid electrolyte, the outer layer, which acts as a diaphragm, on the one hand must be mechanically stable to be able to withstand the rapidly rising pressure of the water vapor, and on the other hand must be sufficiently porous to allow the water vapor to pass from the inside to the outside.

For example, the multi-ply thermal shock protective layer is implemented by a combination of plasma coating and dip coating. In addition, all combinations of plasma coating, dip coating, and spray coating are implementable for producing a multi-ply thermal shock protective layer. The multi-ply thermal shock protection may be achieved by various material compositions, using the same application method, or by using various application methods. For example, the thermal shock protective layer is implemented in a combination of atmospheric plasma spraying and a sol-gel suspension. The sol-gel suspension forms a smooth and finely porous layer on the plasma-sprayed surface. The penetration of water into the plasma-sprayed layer is thus prevented. Due to the water-free plasma-sprayed layer, no heat output for the evaporation of water is required when the sensor element is heated up, as the result of which the fast light-off time may be reduced.

An alternative option for implementing graded thermal shock protection is to apply a highly porous suspension-sprayed layer whose surface is melted by thermal treatment in the flame of a plasma burner in a second step. This results in a reduction in the permeability at the surface of the thermal shock protective layer.

Such multi-ply thermal shock protection may be demonstrated with the aid of optical analysis and polished specimens of a lambda sensor.

DETAILED DESCRIPTION

Figure 1:
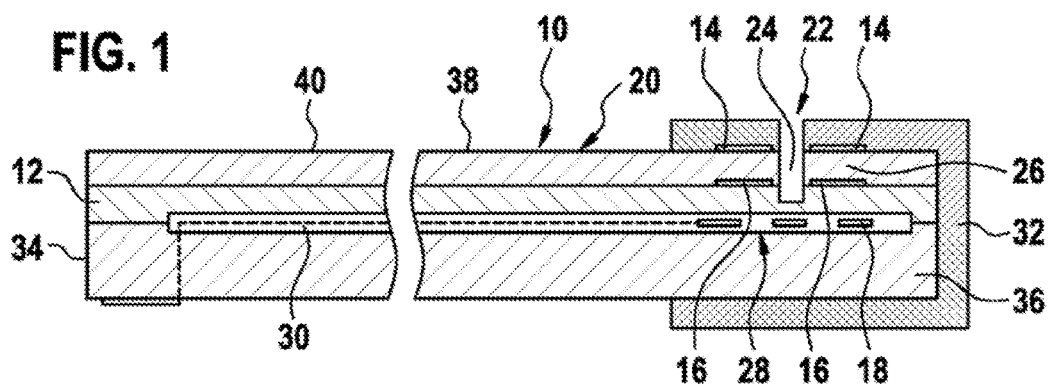
FIG. 1 shows a longitudinal section view of a sensor element according to the present invention.

Sensor element 10 illustrated in FIG. 1 may be used for detecting physical and/or chemical properties of a measuring gas, whereby one or multiple properties may be detected. The present invention is described below in particular with regard to a qualitative and/or quantitative detection of a component of the gas, in particular with regard to a detection of an oxygen content in the measuring gas. The oxygen content may be detected in the form of a partial pressure and/or in the form of a percentage, for example. However, other types of gas components are also detectable in principle, for example nitrogen oxides, hydrocarbons, and/or hydrogen. Alternatively or additionally, however, other properties of the measuring gas are also detectable, such as the temperature, for example. The present invention is usable in particular in the field of automotive technology, so that the measuring gas chamber may in particular be an exhaust tract of an internal combustion engine, and the measuring gas may in particular be an exhaust gas.

Sensor element 10, as an example of a component of a planar lambda sensor, includes a solid electrolyte 12. Solid electrolyte 12 may be made up of multiple solid electrolyte layers or may include multiple solid electrolyte layers. Solid electrolyte 12 may in particular be a ceramic solid electrolyte 12, for example zirconium dioxide ($ZrO_2$), in particular yttrium-stabilized zirconium dioxide (YSZ) and scandium-doped zirconium dioxide (ScSZ), which may contain small additions of aluminum oxide ($Al_2O_3$) and/or silicon oxide ($SiO_2$). Solid electrolyte 12 includes at least one functional element. In the specific embodiment shown, solid electrolyte 12 includes, for example, a first electrode 14, a second electrode 16, and a heating element 18. First electrode 14 is situated on a surface 20 of solid electrolyte 12. Second electrode 16 is situated inside solid electrolyte 12.

In addition, sensor element 10 includes a gas inlet path 22. Gas inlet path 22 includes a gas inlet port 24. First electrode 14 and second electrode 16 surround gas inlet port 24, for example in a ring-shaped manner. For example, second electrode 16 is situated in an electrode cavity, not shown in greater detail, which is connected to gas inlet port 24 via a channel. A diffusion barrier, for example, is situated in the channel which reduces or even prevents a flow of gas from the measuring gas chamber into the electrode cavity and allows only a diffusion. Via the diffusion barrier, second electrode 16 may thus be acted on by gas from the measuring gas chamber. First electrode 14 and second electrode 16 are connected to one another via solid electrolyte 12, and form a pump cell 26. A limiting current of pump cell 26 may be set via the diffusion barrier.

Heating element 18 is situated in solid electrolyte 12, farther in the direction of extension of gas inlet port 24. Heating element 18 is configured for heating pump cell 26, in particular to a temperature at which pump cell 26 is conductive for ions, in particular oxygen ions, for example 750° C. to 900° C. Heating element 18 includes a heating area 28 and connecting lines 30. For example, heating element 18 is designed as an electrical resistance heating element and is connectable to a voltage source with the aid of connecting lines 30.

In addition, solid electrolyte 12 may include a reference gas channel, not shown in greater detail. The reference gas channel may be designed as a macroscopic reference air channel, in which air having a known property, for example an oxygen partial pressure, is present. Alternatively, the reference gas channel may be designed not as a macroscopic channel, but, rather, as a pumped reference, i.e., an artificial reference. A third electrode, for example, is situated in the electrode cavity. For example, second electrode 16 is situated opposite from the third electrode. A fourth electrode may be situated in the reference gas channel, or for a pumped reference may be situated on an insulation layer inside solid electrolyte 12. The third electrode, the fourth electrode, and the portion of solid electrolyte 12 between same forms an electrochemical cell, for example a Nernst cell. With the aid of pump cell 26, a pump current, for example, may be set by pump cell 26 in such a way that the condition λ=1 or some other known composition prevails in the electrode cavity. This composition is in turn detected by the Nernst cell by measuring a Nernst voltage between the third electrode and the fourth electrode. Based on the measured Nernst voltage, the composition in the electrode cavity may be deduced and the pump current may be changed if needed in order to set the condition λ=1. The composition of the exhaust gas may then be deduced, based on the pump current.

The optional Nernst cell in solid electrolyte 12 is preferably provided to measure the particular residual oxygen content in a combustion exhaust gas, so that on this basis, the ratio of combustion air to fuel may be regulated for further combustion in such a way that neither excess fuel nor excess air occurs. Since the temperature is still far below 300° C. for a cold engine, the lambda sensor and therefore the regulation operate very slowly or not at all during a cold start. For this reason, solid electrolyte 12 of sensor element 10 is preferably equipped with electric heating element 18 so that the sensor may already be brought to the required temperature shortly after the cold start. It is thus possible to already ensure an emission-optimized operation in the warm-up phase of the engine. Since the operation of a lambda sensor is well known, for example from the above-mentioned related art, a detailed description of the mode of operation is dispensed with.

Sensor element 10 also includes a thermal shock protective layer 32. Thermal shock protective layer 32 may be made at least partially of a ceramic material. For example, thermal shock protective layer 32 contains porous aluminum oxide. Thermal shock protective layer 32 has a porosity of 50%, for example. Solid electrolyte 12 extends in the measuring gas chamber along a direction of longitudinal extension, which extends from left to right based on the illustration in FIG. 1. As a result, sensor element 10 includes a connection-side end 34 which is on the left, based on the illustration in FIG. 1, and an end 36 on the measuring gas chamber side, which is on the right, based on the illustration in FIG. 1. As shown in FIG. 1, pump cell 26 is situated in the vicinity of end 36 on the measuring gas chamber side. In addition, solid electrolyte 12 includes side surfaces 38, one of which is surface 20, and also includes end-face surfaces, and side edges 40 which join side surfaces 38 together or form a transition between side surfaces 38. Side edges 40 may be rounded, angular, or beveled. Thermal shock protective layer 32 is applied, at least in sections, to solid electrolyte 12. For example, thermal shock protective layer 32 is applied only in one-third of the area in the vicinity of end 36 on the measuring gas chamber side, based on a dimension in the direction of longitudinal extension, and covers all side surfaces there. Based on the illustration in FIG. 1, thermal shock protective layer 32 thus has a U-shaped cross section. In particular, thermal shock protective layer 32 covers first electrode 14, whereby a porous ceramic electrode protective layer may be provided between first electrode 14 and thermal shock protective layer 32. It is emphasized that gas inlet port 24 is not closed off by thermal shock protective layer 32, but instead has free access to the measuring gas chamber. Alternatively, thermal shock protective layer 32 may also completely cover all side surfaces 38, or may cover only first electrode 14 and gas inlet port 24. The exact location at which thermal shock protective layer 32 is situated may be selected as a function of the particular use or site of operation of sensor element 10. Based on the manufacturing method according to the present invention, which is described in greater detail below, thermal shock protective layer 32 may have a thinner design than in conventional sensor elements from the related art. In addition, for thicknesses which remain the same, improved thermal shock protection and quicker operational readiness may be achieved compared to conventional sensor elements. Thus, for example, a first highly porous layer of 200 μm may be applied to the sensor element, followed by a 50-μm low-porosity layer. The thermal shock protective layer customarily has a thickness of approximately 300 μm in conventional sensor elements from the related art. In contrast, thermal shock protective layer 32 according to the present invention may have a thickness of less than 300 μm, for example a thickness of 150 μm to 300 μm, preferably a thickness of 200 μm to 280 μm, for example 250 μm. The thicknesses stated above indicate the overall thickness of the thermal shock protective layer; the thickness ratios between the individual layers may vary in any proportions.

Figure 2:
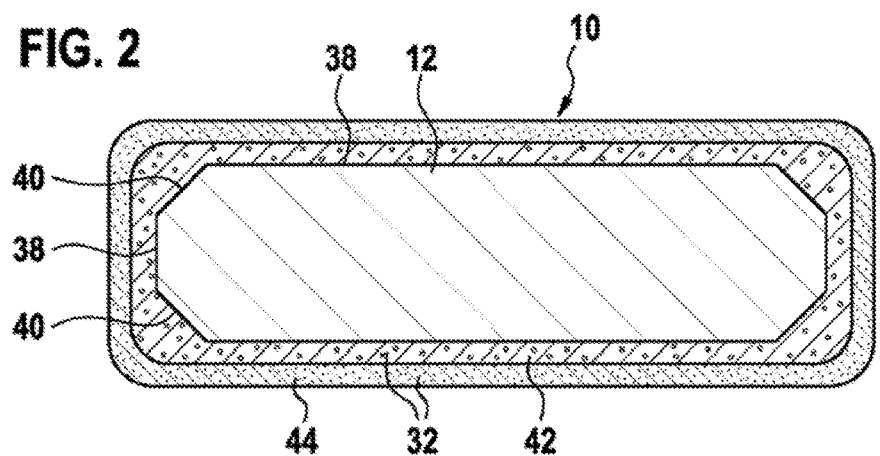
FIG. 2 shows a cross-sectional view of a sensor element according to the present invention in the area of a gas inlet port.

FIG. 2 shows a cross-sectional illustration of sensor element 10 perpendicular to the direction of longitudinal extension of sensor element 10. As is apparent from the illustration in FIG. 2, thermal shock protective layer 32 is formed from a first layer 42 made of a ceramic material and a second layer 44 made of a ceramic material. First layer 42 is situated on solid electrolyte 12. In the section plane of FIG. 2, first layer 42 surrounds solid electrolyte 12 on all sides, and thus completely covers side surfaces 38 and side edges 40, viewed in the section plane of FIG. 2. Second layer 44 is situated on first layer 42. Second layer 44 surrounds first layer 42 on all sides in the section plane of FIG. 2. First layer 42 is thus situated between solid electrolyte 12 and second layer 44. First layer 42 has a first porosity. For example, first layer 42 has a first porosity of 40% to 80%, for example 50%. Second layer 44 has a second porosity. For example, second layer 44 has a second porosity of 10% to 20%, for example 15%. First layer 42 differs from second layer 44 with respect to at least one material property. The material property is selected from the group composed of: porosity, heat conductivity, coefficient of thermal expansion, heat capacity, and wettability. According to the above statements, the first porosity is greater than the second porosity. It is explicitly emphasized that first layer 42 and second layer 44 may be produced in such a way that a continuous transition of the porosity between these layers, and thus a porosity gradient, is formed. First layer 42 may be thicker than second layer 44. For example, first layer 42 has a thickness of 170 μm, and second layer 44 has a thickness of 80 μm.

First layer 42 and second layer 44 may be made of identical materials which are treated differently during the production, as described in greater detail below. Alternatively, first layer 42 and second layer 44 are made of different materials. In addition, layers may be made of different materials, which are treated in the same way during the production, for example by using the same application method or application process. For example, first layer 42 is made at least partially of zirconium dioxide, and second layer 44 is made at least partially of aluminum oxide. First layer 42 therefore has a lower heat capacity than second layer 44. The thermal properties, for example heat conductivity, thermal expansion, and heat capacity, may be set partially independently of the porosity by using different ceramics for first layer 42 and second layer 44.

Figure 3:
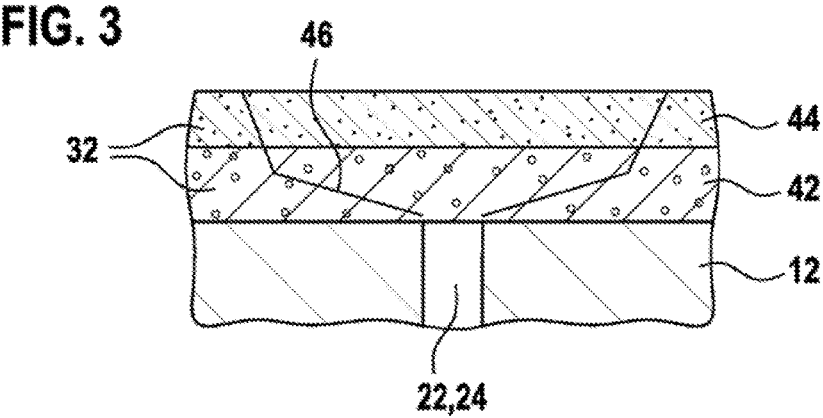
FIG. 3 shows an enlarged cross-sectional view of a sensor element according to the present invention in the area of a gas inlet port.

FIG. 3 is an enlarged cross-sectional view of sensor element 10 in the area of gas inlet port 24. An inlet area for the measuring gas to gas inlet port 24 is provided via a line 46. As the result of the first porosity of first layer 42 being greater than the second porosity of second layer 44, the inlet area within first layer 42 is greatly enlarged, but its surface area becomes only slightly larger within second layer 44 due to the lower second porosity.

Figure 4:
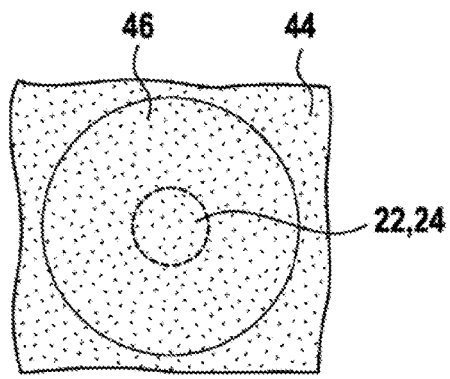
FIG. 4 shows a top view onto a sensor element according to the present invention in the area of a gas inlet port.

FIG. 4 is a top view of sensor element 10 in the area of gas inlet port 24. The greatly enlarged surface area of inlet area 46 is readily apparent. Accordingly, the high porosity of first layer 42 represents a very good thermal insulation between solid electrolyte 12 and second layer 44, since the heat conductivity is low compared to solid electrolyte 12 due to the high proportion of pores which contain a large quantity of air. Solid electrolyte 12 may therefore be heated up more quickly; i.e., a shorter fast light-off time is achieved, since the mass of thermal shock protective layer 32 is thermally decoupled from solid electrolyte 12. The decoupling of the thermal masses of thermal shock protective layer 32 from solid electrolyte 12 also results in a lower heating voltage requirement, since the cooling of thermal shock protective layer 32 is not directly transferred to the surface of solid electrolyte 12. A smooth surface with less roughness is achieved by setting a fine or low porosity of second layer 44. This prevents the penetration of water into second layer 44, which would increase the fast light-off time. There is also an improved thermal shock robustness on account of the reduced water permeability due to producing a smooth surface. To allow water which has penetrated into thermal shock protective layer 32 to be able to escape during rapid heat-up of solid electrolyte 12, second layer 44, which acts as a diaphragm, on the one hand is mechanically stable, due to the manufacturing method described below, in order to be able to withstand the rapidly rising pressure of the water vapor, and on the other hand is sufficiently porous to allow the water vapor to pass from the inside to the outside. In particular, the feed area or inlet area 46 of gas inlet port 24 of sensor element 10 is significantly enlarged by roughly porous, inner or first layer 42 of thermal shock protective layer 32, and therefore the gas inlet restriction by outer or second, comparatively more dense layer 44 is effectively decreased. For a manufacturing variation of the permeability of first layer 42, this results in even smaller variations in the gas inlet, and thus the increase of the characteristic curve of sensor element 10.

Sensor element 10 may be manufactured according to the present invention as follows. Initially, a solid electrolyte 12 which includes above-mentioned functional elements 14, 16, and 18 is provided. For example, solid electrolyte 12 is made of multiple solid electrolyte layers, which together with the above-mentioned functional elements, i.e., with first electrode 14, second electrode 16, and heating element 18, are printed in a manner known per se. Examples of known techniques are the so-called film technique or multi-ply technique. Solid electrolyte 12 is subsequently sintered together with first electrode 14, second electrode 16, and heating element 18. The sintering may take place, for example, at a temperature between 1,350° C. and 1,550° C., in particular at 1,385° C., the temperature being held constant for 5.5 hours, for example. This type of design of a planar sensor element 10 is well known from the above-mentioned related art, so that a more detailed discussion is dispensed with.

In addition, a first thermal shock protective layer 42 is applied by plasma spraying, whereby various metal oxides, for example aluminum oxide and zirconium dioxide, may be used. A second thermal shock protective layer 44 having a lower porosity is subsequently applied to first layer 42, for example by dipping or spraying. The penetration of water into plasma-sprayed first layer 42 is thus prevented. Due to water-free plasma-sprayed layer 42, no heat output for the evaporation of water is required when sensor element 10 is heated up, as the result of which the fast light-off time may be reduced.

A sol made of at least one precursor of a ceramic material, for example, may be provided for second layer 44. The precursor may be selected from the group composed of a precursor of aluminum oxide, zirconium dioxide, and titanium oxide. In addition, ceramic particles made of one or multiple of the above-mentioned metal oxides, having a diameter of 0.03 µm to 3.0 µm, preferably 0.05 µm to 2.0 µm, for example 0.5 µm or 1.0 µm, are dispersed in the sol as a filler. In addition, the sol may include at least one pore-forming agent such as coal dust. Both thermal shock protective layers 42 and 44 are applied, at least in sections, to sintered solid electrolyte 12.

The application of the sol is followed by a thermal treatment step of solid electrolyte 12. The thermal treatment step is carried out at a temperature of 40° C. to 120° C., preferably 50° C. to 100° C., for example 75° C. The thermal treatment step may be carried out for a period, for example, of 5 minutes to 30 minutes, for example for 12 minutes, at 50° C. This results in crosslinking of the organic components in the sol.

At least one annealing step of solid electrolyte 12 is subsequently carried out after the sol is applied. The annealing step may be carried out at a temperature of 1,000° C. to 1,300° C., preferably 1,100° C. to 1,200° C., for example 1,150° C. For example, the annealing step is carried out for less than 10 minutes. The annealing step may be carried out by an external device or by heating element 18. For example, a voltage is applied to heating element 18, thus heating it.

Due to the annealing step, the organics in the sol are oxidized, and solid bridges form between the particles of the precursors of the ceramic material, which result from oxidation of the organometallic precursors as well as from sintering of the ceramic particles. Carrying out the annealing step with the aid of heating element 18 may be advantageous, since this ensures better outgassing of the oxidation products of the organic components. The pore-forming agent combusts as a result of the annealing step, so that the first porosity, for example a porosity of 50%, is formed in ceramic first layer 42 formed from the sol. This ensures that the gas phase processes, for example diffusion, change only slightly compared to conventional sensor elements. The porosity may be set by a suitable selection and type of the sol, the ceramic filler particles, and the pore-forming agent. It is explicitly emphasized that even higher porosities of 55%, 60%, or 70%, for example, may be achieved in this way.

To prevent penetration of the coating materials into gas inlet port 24 and ensure thermal shock robustness of gas inlet port 24, there is the option, prior to applying the thermal shock protective layers, of applying a porous ceramic layer with the aid of screen or stencil printing via gas inlet port 24 and subsequently sintering solid electrolyte 12. The thermal shock protective layers are subsequently applied, achieving closure of porously covered gas inlet port 24.

Alternatively, the above-described dipping or spraying process of a sol-gel solution may also be used in order to produce multiple layers having different porosities, using this application method. The porosity is set by a suitable selection and type of the sol, the ceramic filler particles, and the pore-forming agent. For example, a higher proportion of the pore-forming agent is used for a first layer 42, compared to the sol for second layer 44.

Second layer 44 of the sol is applied to first layer 42, first layer 42 having a greater porosity than second layer 44 after the annealing step. Second layer 44 is applied, for example, in such a way that after production it has the above-mentioned thickness, for example a thickness of 50 µm. In this way, for example, thermal shock protective layer 32, which has a gradient of the porosity, may be made up of multiple layers. More than two layers may also be applied. For example, layers are repeatedly applied with subsequent thermal treatment. When all desired layers have been applied, they are annealed together. Alternatively, the annealing step may be carried out after each thermal treatment of a layer.

It is possible to apply the sol for first layer 42 and/or second layer 44 in such a way that the sol is thicker on side edges 40 than on side surfaces 38. A greater layer thickness on side edges 40 may be achieved by removal of the undried suspension from side surfaces 38 and a targeted application on side edge 40. This is achievable, for example, by targeted setting of the rheological properties of the suspension, i.e., by multiple applications of the sol. Alternatively or additionally, a greater layer thickness on side edges 40 may be achieved by better wetting of the side edges by changing the edge grinding of solid electrolyte 12; for example, beveled cylindrical grinding or multiple facet grinding is carried out on side edges 40.

In addition, various application methods such as spraying, dipping, thermal spraying, in particular plasma spraying, printing processes such as screen printing or stencil printing, and doctor blade coating methods may be used to produce the individual thermal shock protective layers. In addition, layers made of different materials may be produced, which during production are treated in the same way, for example by using the same application method. In addition, the layers may be applied to the sintered or unsintered sensor element.

Figure 5:
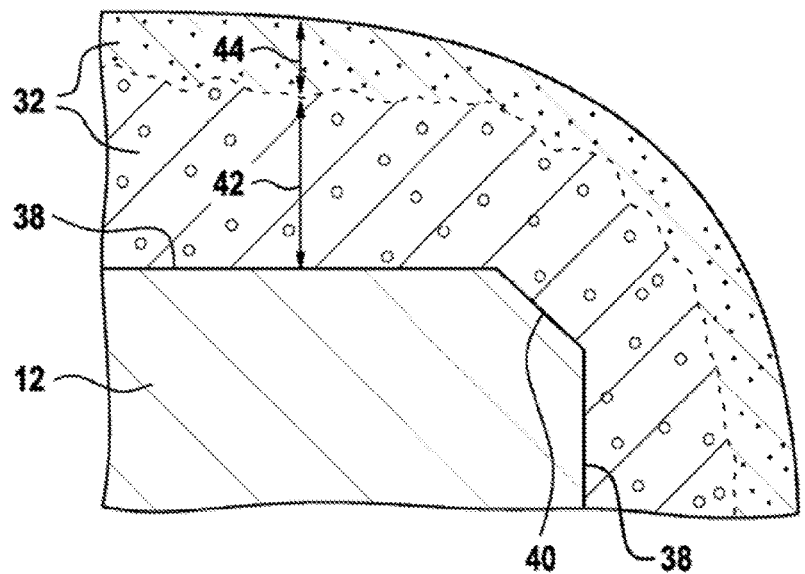
FIG. 5 shows an enlarged illustration of a detail of a sensor element according to the present invention in the area of a side edge, which includes the thermal shock protective layer.

FIG. 5 shows an enlarged illustration of a detail of sensor element 10 according to the present invention in the area of a side edge 40 which includes thermal shock protective layer 32, which is made of a plasma-sprayed first layer 42 and a second layer 44 made of the sol described above. It is apparent that first layer 42 is thicker than second layer 44. For example, first layer 42 has a thickness of 170 µm, and second layer 44 has a thickness of 80 µm.

Another alternative option for implementing a graded thermal shock protective layer 32 is to apply a highly porous suspension-sprayed first layer 42 which has a thickness of 250 µm, for example, and which according to the manufacturing method described above is thus thicker than first layer 42. The surface of first layer 42, i.e., the side facing away from solid electrolyte 12, is melted in a second step by thermal treatment in the flame of a plasma burner. The distance from the plasma burner, whose plasma may have a temperature of 10,000° C. to 20,000° C., is set in such a way that the temperature on the surface of first layer 42 is approximately 2,000° C. This results in a reduction in the permeability at the surface of thermal shock protective layer 32, and second layer 44 is formed from first layer 42.

What is claimed is:

1. A method for manufacturing a sensor element for detecting at least one property of a measuring gas in a measuring gas chamber, comprising:
   providing at least one solid electrolyte that includes at least one functional element;
   applying, at least in sections, a first ceramic layer to the solid electrolyte, the first ceramic layer having a first porosity after the application; and
   after applying the first ceramic layer to the solid electrolyte, applying, at least in sections, a second ceramic layer, the second ceramic layer having a second porosity after the application, and the first ceramic layer differing from the second ceramic layer with respect to at least one material property;
   wherein at least one of the first ceramic layer and the second ceramic layer is made of a sol, the sol being a colloidal dispersion composed of precursors of metal oxides;
   wherein the second ceramic layer is situated on the first ceramic layer, the second ceramic layer together with the first ceramic layer forming a thermal shock protective layer;
   wherein the thermal shock protective layer is applied only on one third of the solid electrolyte relative to a longitudinal direction of the solid electrolyte, and being applied at a measuring gas side end of the solid electrolyte, and covering all lateral surfaces of the solid electrolyte at the measuring gas side end; and
   wherein the second ceramic layer is less porous and less thick than the first ceramic layer.

2. The method as recited in claim 1, wherein the sensor element is for detecting one of a proportion of a gas component in the measuring gas and a temperature of the measuring gas.

3. The method as recited in claim 1, wherein the material property corresponds to one of porosity, heat conductivity, coefficient of thermal expansion, heat capacity, wettability, and thermal shock protection.

4. The method as recited in claim 1, wherein the first ceramic layer and the second ceramic layer are made of different ceramic materials.

5. The method as recited in claim 1, wherein the first ceramic layer has a lower heat capacity than the second ceramic layer.

6. The method as recited in claim 1, wherein at least one of the first ceramic layer and the second ceramic layer is applied by one of plasma spraying, spraying, dipping, a printing method, and a doctor blade coating method.

7. The method as recited in claim 1, wherein at least one of the first ceramic layer and second ceramic layer is applied to the sensor element after sintering.

8. The method as recited in claim 1, wherein at least one of the first ceramic layer and second ceramic layer is applied to the sensor element before sintering.

9. The method as recited in claim 1, further comprising performing at least one thermal treatment step of the solid electrolyte after the sol is applied to convert the sol to metal oxides.

10. The method as recited in claim 1, further comprising annealing the solid electrolyte after the sol is applied.

11. The method as recited in claim 10, wherein the solid electrolyte includes a heating element for heating the solid electrolyte, and wherein the heating element carries out the annealing step, and wherein the sol is converted to metal oxides based on the heating.

12. The method as recited in claim 1, wherein the first ceramic layer is applied with the aid of atmospheric plasma spraying.

13. The method as recited in claim 1, wherein the second ceramic layer is applied by thermal treatment of a surface of the first ceramic layer facing away from the solid electrolyte.

14. The method as recited in claim 13, wherein the thermal treatment includes melting.

15. The method as recited in claim 1, wherein the precursors of metal oxides include at least one of metal alcoholates and metal carboxylates.

* * * * *